(12) United States Patent
Brandinger et al.

(10) Patent No.: US 6,566,627 B2
(45) Date of Patent: May 20, 2003

(54) LASER METHOD FOR SHAPING OF OPTICAL LENSES

(75) Inventors: Jay J. Brandinger, Pennington, NJ (US); Brian D. Hoffman, Princeton, NJ (US); Edward T. Polkowski, Lloyd Harbor, NY (US)

(73) Assignee: Westar Photonics, Inc., Pennington, NJ (US)

( * ) Notice: Subject to any disclaimer, the term of this patent is extended or adjusted under 35 U.S.C. 154(b) by 0 days.

(21) Appl. No.: 09/925,067

(22) Filed: Aug. 7, 2001

(65) Prior Publication Data

US 2002/0049511 A1 Apr. 25, 2002

Related U.S. Application Data

(60) Provisional application No. 60/224,647, filed on Aug. 8, 2000.

(51) Int. Cl.[7] .............................................. B23K 26/38
(52) U.S. Cl. .................... 219/121.69; 264/400; 700/166
(58) Field of Search ...................... 219/121.68, 121.69; 700/166; 264/400

(56) References Cited

U.S. PATENT DOCUMENTS

| | | | |
|---|---|---|---|
| 4,307,046 A | 12/1981 | Neefe | |
| 4,508,749 A | 4/1985 | Brannon et al. | |
| 4,665,913 A | 5/1987 | L'Esperance, Jr. | |
| 4,729,372 A * | 3/1988 | L'Esperance, Jr. | |
| 5,108,388 A | 4/1992 | Trokel | |
| 5,236,551 A | 8/1993 | Pan | |
| 5,256,853 A * | 10/1993 | McIntyre | 219/121.69 |
| 5,350,374 A | 9/1994 | Smith | |
| 5,624,437 A * | 4/1997 | Freeman et al. | |
| 5,777,719 A * | 7/1998 | Williams et al. | |
| 5,851,328 A | 12/1998 | Kohan | |
| 5,936,757 A * | 8/1999 | Kim et al. | |
| 6,074,579 A | 6/2000 | Greshes | |
| 6,095,651 A * | 8/2000 | Williams et al. | |
| 6,315,413 B1 * | 11/2001 | Shimmick et al. | |
| 6,338,559 B1 * | 1/2002 | Williams et al. | |
| 6,413,251 B1 * | 7/2002 | Williams | |
| 2001/0045690 A1 * | 11/2001 | Brandinger | |

FOREIGN PATENT DOCUMENTS

WO  WO-92-01417 A1 *  2/1992
WO  WO-01-12114 A1 *  8/2000

* cited by examiner

Primary Examiner—Geoffrey S. Evans
(74) Attorney, Agent, or Firm—Woodbridge & Associates, P.C.; Richard C. Woodbridge, Esq.

(57) ABSTRACT

A method for making accurate and precise customized corrections to the surface of an optical lens is described. An electronic correction contour is generated from a measured refractive correction for a patient, and transferred to the surface of the lens by ablation etching with one or more laser pulses. After each of the laser pulses, the refractive properties of the lens are measured and compared to the electronic contour correction derived from a patient's refractive correction. The ablation etching is terminated in localized areas where the refractive properties match the electronic correction contour. End point detection includes monitoring refractive qualities of the lens during the recontouring process, modifying the pattern through changes in the laser pulses.

9 Claims, 12 Drawing Sheets

LASER PATTERNING USING TRANSMISSIVE OR REFLECTIVE MASK

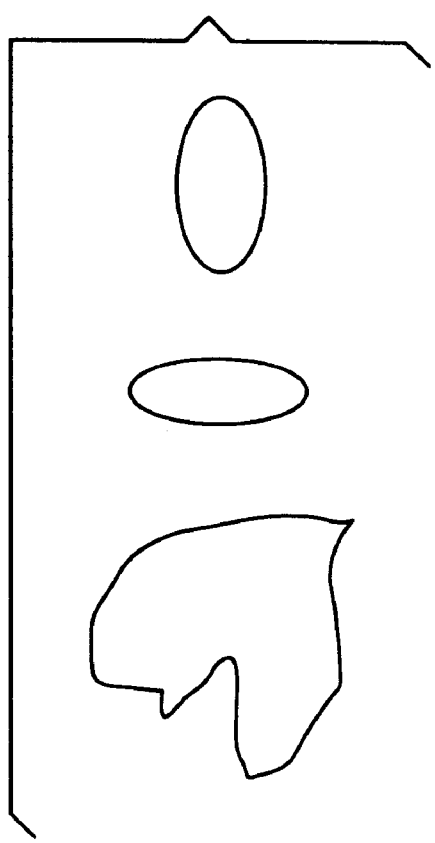

LASER METHOD FOR SHAPING OF OPTICAL LENSES

CROSS REFERENCE TO RELATED APPLICATIONS

This application claims the priority of U.S. Provisional Application Serial No. 60/224,647 entitled "A Laser Beam Patterning Device and Apparatus for Reshaping of Eyeglass Lenses by Ablation and Continuous Process Monitoring" filed on Aug. 8, 2000 the entire contents and substance of which are hereby incorporated in total by reference.

BACKGROUND OF THE INVENTION

1. Field of the Invention

This invention relates to a laser method for rapid and accurate shaping of optical lenses.

2. Description of Related Art

The use of ablation etching to pattern polymeric material is well known in the art. In U.S. Pat. No. 4,508,749, for example, Brannon et al. discloses an ultraviolet radiation based method for etching patterns in polyimide layers located on integrated circuit substrates, and subsequently depositing an electrical circuit pattern thereover to form electrical interconnections to elements of the integrated circuit. In U.S. Pat. No. 5,236,551, Pan describes a laser-based photoablative etching process for patterning a polymeric film which is subsequently used as a mask for chemical etching of patterns in an underlying metal layer.

Optical lenses produced from polymeric substances such as polycarbonate are well known in the art, and many standard molded lenses are items of commerce. Kohan, in U.S. Pat. No. 5,851,328, and Greshes in U.S. Pat. No. 6,074,579, among others, describe moulding methods for the manufacture of such plastic optical elements. Companies such as Vision-Ease Lens, Inc. of St. Cloud, Minn., and Optical Polymer Research, Inc. of Gainesville, Fla. manufacture polymers and polymer based lenses in a variety of shapes, sizes and optical densities. The lenses are molded for standard patient correction factors such as spherical, aspherical and astigmatic disorders.

Vision care instrumentation for measuring refractive error in a patient are manufactured by several companies such as Bausch and Lomb Vision Care of Rochester, N.Y. and Zeiss Humphrey Systems of Dublin, Calif. These systems have been commercially available for decades.

Instrumentation for measuring refractive corrections for lenses are available from companies such as Neitz Instruments Co. of Tokyo, Japan and Optikos Corporation of Cambridge, Mass. State-of-the-art instrumentation has the ability to measure lens contour to a surface height accuracy of 0.001 mm.

Although correction factors for a patient can be determined with a great deal of accuracy and precision, commercial lenses are provided with standard corrections which do not necessarily fit a given patient's individuals needs. Custom ground lenses are prohibitively expensive for most patients, as the process of custom grinding requires a highly skilled optician, with experience in lens reshaping. As a result, most patients must accept the standard correction lenses that are available, and consequently do not achieve optimum visual acuity.

Smith, in U.S. Pat. No. 5,350,374 discloses an apparatus and method for performing either photorefractive keratectomy or phototherapeutic keratectomy on the anterior surface of the cornea of the eye using a feedback controlled segmented laser beam.

Neefe, in U.S. Pat. No. 4,307,046 teaches that infrared lasers may be used as the cutting means for shaping a lens. Because the lens is rotated on a spindle in this method, however, the corrected surface is limited to a contour which is concentric with the spindle center.

It is clear from the foregoing analysis that a serious need exists for an economical method for recontouring optical lens surfaces so that correction factors more accurately reflect individual refractive corrections of patients. Such a customized three-dimensional contouring method is not taught in the prior art.

SUMMARY OF THE INVENTION

Briefly described, the invention comprises a method for making accurate and precise customized corrections to the surface of an optical lens. An electronic correction contour is generated from a measured refractive correction for a patient, and transferred to the surface of the lens by ablation etching with one or more laser pulses. After each of the laser pulses, the refractive properties of the lens are measured and compared to the electronic contour correction derived from a patient's refractive correction. The ablation etching is terminated in localized areas where the refractive properties match the electronic correction contour.

The invention may be more fully understood by reference to the following drawings.

BRIEF DESCRIPTION OF THE DRAWING

FIG. 8 illustrates three different complex patterns which can be created.

DETAILED DESCRIPTION OF PREFERRED EMBODIMENT

During the course of this description like numbers will be used to identify like elements according to the different views that illustrate the invention.

Figure 1:
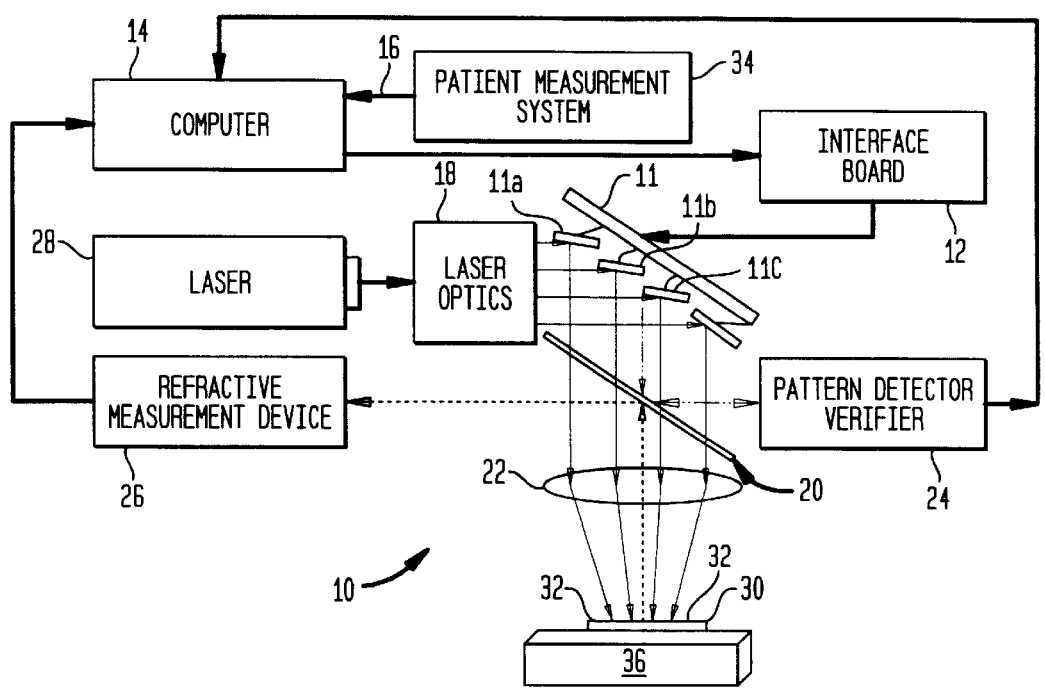
FIG. 1 is a schematic diagram of an apparatus in a preferred embodiment of the method of the present invention.

FIG. 1 shows a schematic diagram of a laser beam apparatus of use in a preferred embodiment of the method of the present invention. The apparatus includes a laser beam modifying system 11, an interface board 12, a computer 14, a computer input 16, laser optics 18, beam splitter 20, re-imaging optics 22, pattern detector and verifier 24, refractive measurement device 26, a laser 28, a index marks 34, a patient measurement system 34, and an XY table 36.

Figure 2A:
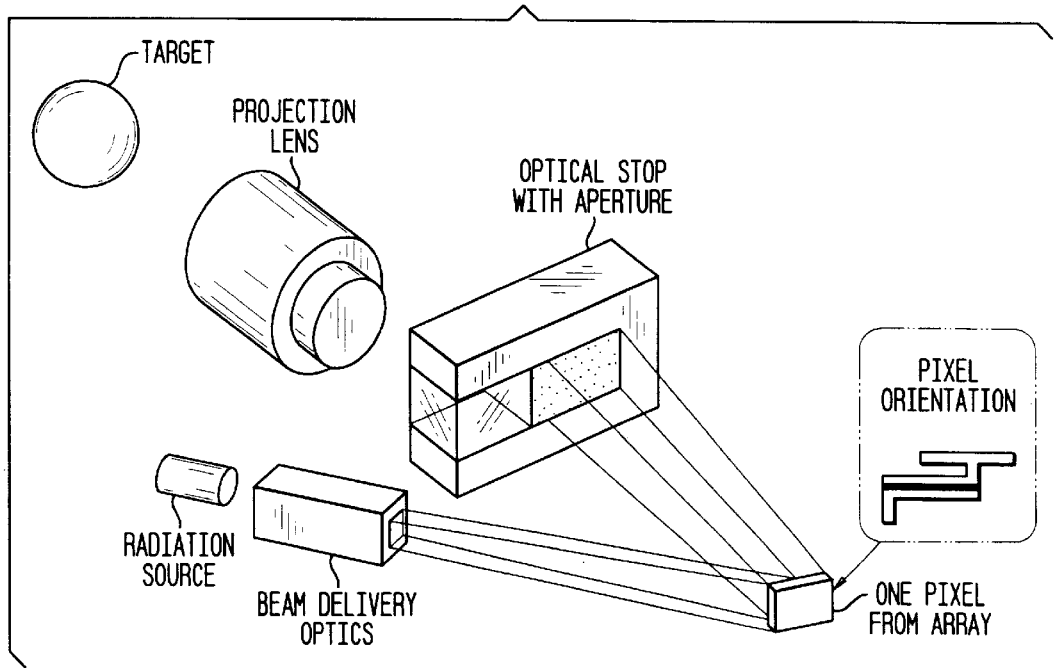
FIG. 2 illustrates the operation of a single undeflected micromirror.
Figure 2B:
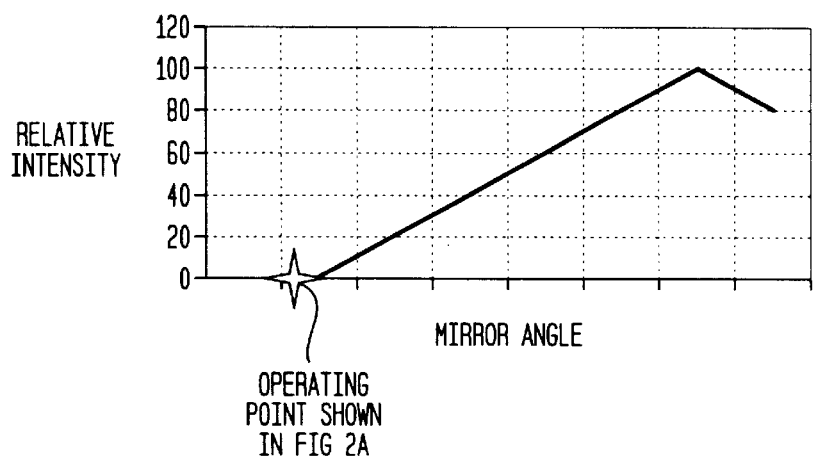
Figure 4:
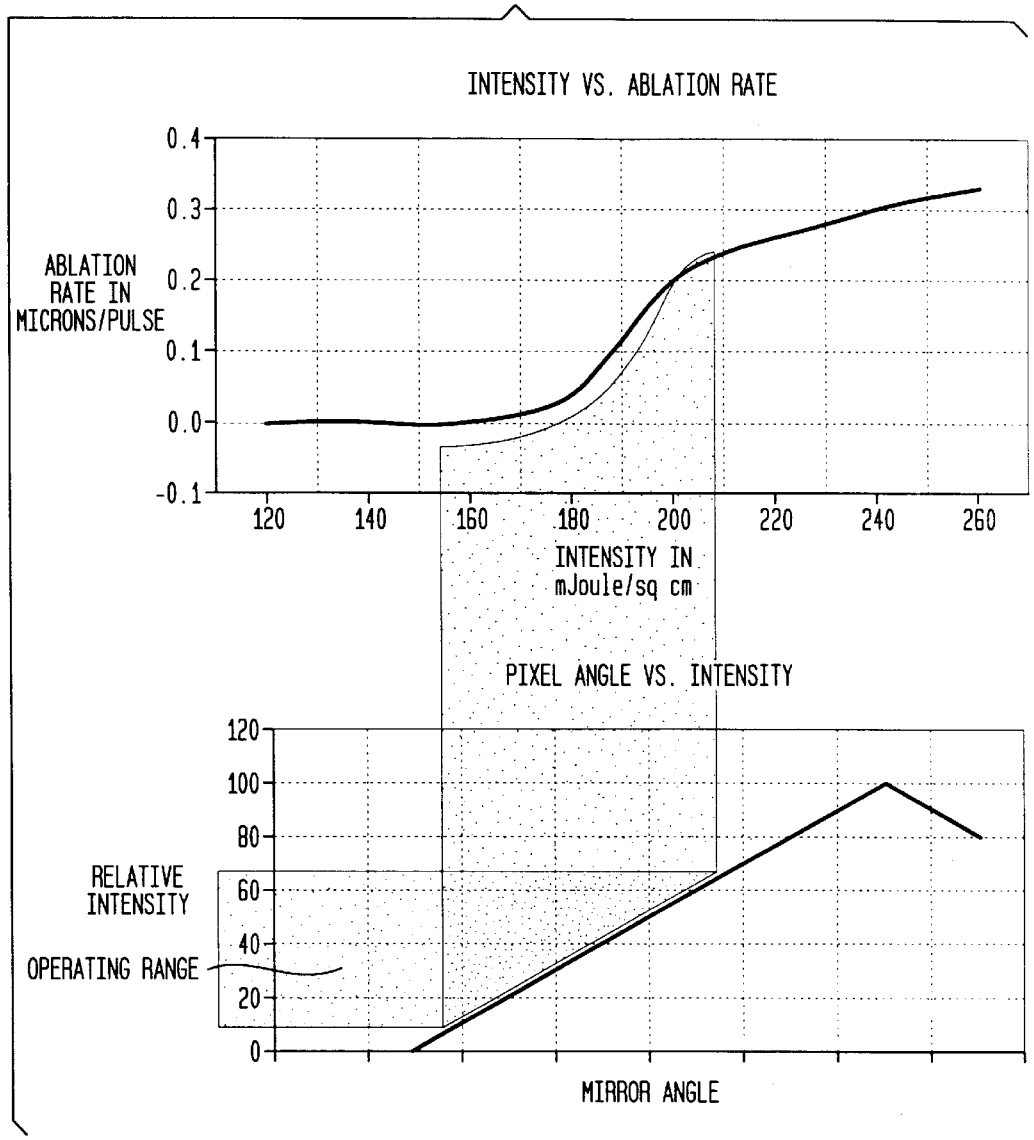
FIG. 4 illustrates the relationship between intensity and ablation rate.

In the preferred embodiment of this invention, the laser modifying system 11 is a thin-film micromirror array as illustrated in FIG. 1. Thin-film micromirror 11 has a plurality of individual micromirrors 11$a,b,c$ . . . , each of which can be individually tilted with respect to incident laser beamlets. In actual practice, a laser beam emanating from laser 28 is split into a plurality of laser beamlets by laser optics 18, and then modulated and reflected by individual micromirrors 11$a,b,c$ . . . through re-imaging optics 20 onto the surface of lens 30. Individual control of the tilting of each micromirror 11$a,b,c$ . . . allows for modulation of the energy of each beamlet before reflection onto the surface of lens 30. When the mirror is not tilted, the laser energy is substantially blocked from the imaging optics 22. As the mirror angle increases the amount of energy directed toward the workpiece is increased, reaching a maximum at maximum tilt angle. The amount of energy that passes through to the lens 30 is linearly proportional to the tilt angle of each mirror as illustrated in FIGS. 2$a,b$ (not tilted) and 3$a,b$ (partially tilted). FIG. 4 is a graph illustrating the relationship between energy intensity and typical ablation rate.

The orientation of each individual micromirror 11$a,b,c$ . . . is controlled by input 16 from computer 14 via an interface board 12, to create a plurality of reflected beamlets having a defined spatial energy density distribution pattern. A series of different patterns can be sequentially imaged onto lens 30 to achieve a desired ablation pattern.

Figure 5:
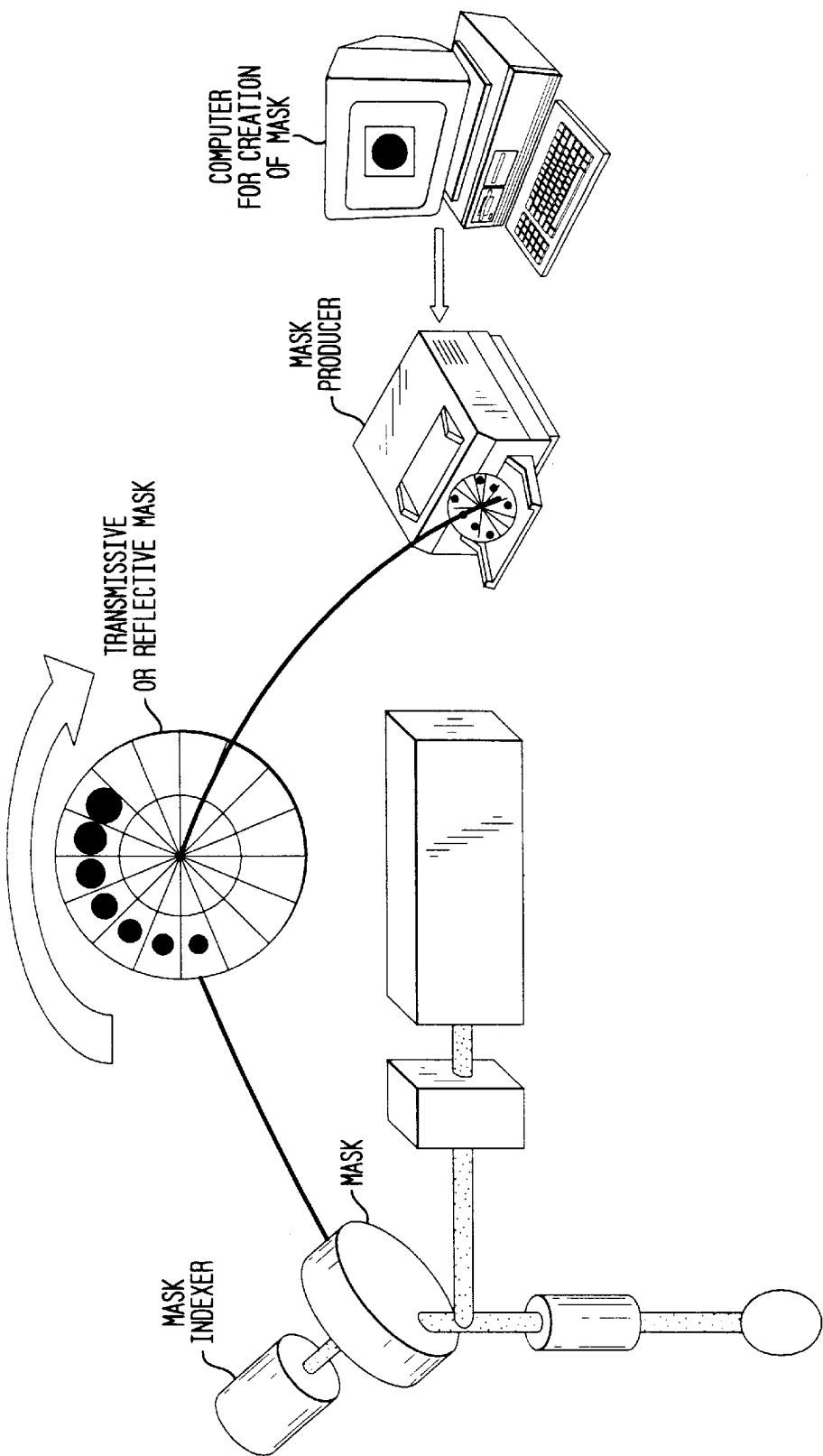
FIG. 5 depicts an alternative pattern generator using a transmissive or reflective mask.

Alternatively, the laser beam modifying system 11 may employ a transmissive or printed reflective mask 38 to generate the custom patterns required to re-contour a lens, as illustrated in FIG. 5. Transmissive masks, which block undesired energy and transmit a desired energy pattern onto the object to be re-contoured, are well known in the art. A printed reflective mask uses a mirror (suitable at the given laser wavelength) with an absorptive pattern, printed or deposited on the mirror surface. In those areas where the mirror is not covered with absorptive material, energy is reflected to the object. In those areas where the absorptive material is present, little or no energy is reflected. The resulting energy pattern produces the desired re-contouring of the object's surface. Through the use of a mirror with many randomly accessible patterns, the same refractive measurement system may be used to select the desired pattern to correct for deviations in the re-contouring process, ultimately achieving the desired end-point correction.

Figure 6A:
FIG. 6*a* depicts a cross section of a lens prior to ablation etch patterning
Figure 6B:
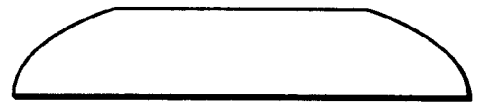
FIG. 6*b* illustrates is similar to FIG. 6*a* with the first layer pattern etched to the second layer.
Figure 6C:
FIG. 6*c* is continues the process with additional patterns etched through the material to the final corrective contour.

Yet another alternative for producing a 3-dimensional contour, involves the use of a positioning table, which moves the lens beneath a small beam. A laser spot beam is used to remove material at each specified position across the lens surface. The system computer coordinates the positioning table with the trigger of the laser. A schematic representation of the lens contouring process of the present invention is illustrated in FIGS. 6$a$–6$c$. FIG. 6$a$ depicts a standard molded lens manufactured from polycarbonate or similar transparent plastic. FIGS. 6$b$ and 6$c$ illustrate successive ablations patterned by the laser modifying system 11. Each laser pulse results in a fixed degree of material removal, dependent upon the system fluence level. Typically, 0.1 to 0.3 microns of material are removed for fluence levels of 100 to 300 mJ/cm$^2$. After each successive energy exposure, the lens is measured to determine the extent to which the correction is being achieved. Real time corrections to pattern generated by laser modifying system 11 are made to ensure that the desired endpoint contour is achieved.

The patient measuring system may use any number of techniques (such as wave front analysis) to create an initial refractive error function for the patient. The system computer uses this input to create a corrective contour to be etched into a standard contour lens. The desired corrective contour is analyzed by the computer to create a recontouring program for the lens. This program is based upon the energy source, the contour error (relative to an existing lens and the patient's need) and the lens material. The computer directs the laser and pattern generator (Mirror Array or other mask type system) to remove lens material with each pulse-pattern of the laser.

Typical end point detection processes known in the art and of use in the present invention include:

1) establishing ablation time/pulses versus depth for specific deposited materials in the layers,
2) establishing depth of the ablated layer optically between laser pulses using surface reflection as compared with the measurement of the layer depth in unablated areas,
3) establishing changes in reflectivity at the boundary of dissimilar layer materials,
4) measuring the amount of material removal by measuring its re-deposition on another substrate,
5) measurement of changes in material composition spectroscopically,
6) using separately deposited layer materials with the same thickness and composition as that used on the work piece overlaying metallic base materials to monitor the ablation etch process.

Figure 7:
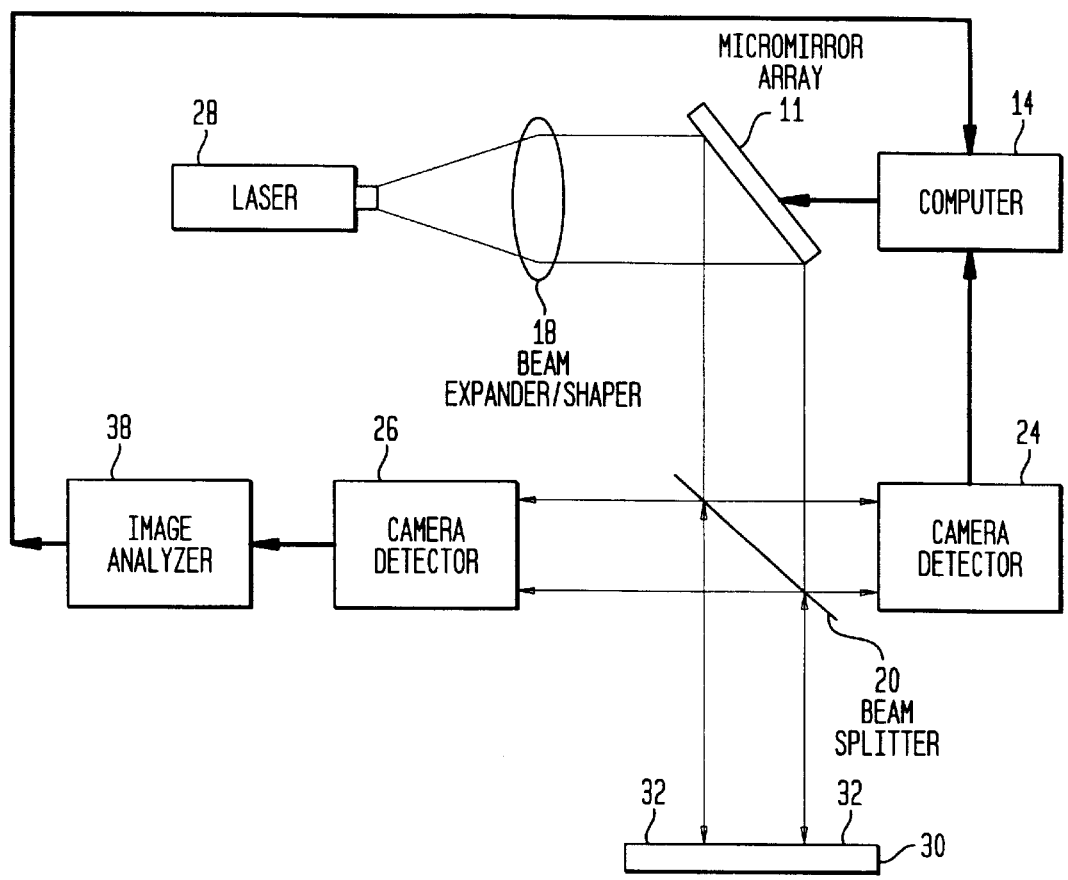
FIG. 7 is a schematic diagram depicting a electronic tracking system.

FIG. 7 illustrates a particular embodiment of the invention that accomplishes two dimensional translation of an energy source to track changes in the desired location of the energy application. The tracking technique includes a method for identifying the location of the desired position for application of the energy and feeding back that location to the two dimensional tracking device. Separately, the energy source is shaped to produce the desired pattern for energy application at the desired location as described above in relation to FIG. 1.

As shown in FIG. 7, the output of laser 28 is passed through a beam expander/homogenizer 18 to fill the field of the two dimensional micromirror array 11, an area larger than the desired energy application area imaged on the lens 30. The computer 14 sets only a portion of the micromirrors in the array to fill the desired two-dimensional shape required with the predetermined energy distribution. Alternate outline shapes of patterns on the work piece can be simple or complex and the energy distribution within boundaries of these patterns may be simple or complex as illustrated in FIG. 8.

The patterned image generated by micromirror 11 is passed through the beam splitter 20 to the lens 30. The reflected image pattern from the workpiece is reflected by the beam splitter 20 a the camera detector 26 which in turn feeds an image analyzer 38. The work piece index marks 32 are also seen by the camera detector 26 and are similarly available to the image analyzer 38. The image analyzer 38 establishes the relative position of the workpiece 30, index marks 32, and an energy pattern such as one depicted in FIG.

8. If the lens 30 shifts its position, the relative position of the workpiece index marks 32 and the energy pattern changes. This location change information is fed to computer 14, which in turn resets the micromirror array 11 to reposition the energy pattern on the lens 30 to reduce the displacement relative to the work piece index marks to an acceptably small error or zero. Camera detector 24 feeds the computer 14, the image of the micromirror array 11, from the beam splitter 20, to analyze and confirm the position and predetermined energy pattern integrity.

It should be noted that this electronic tracking system and pattern shaping invention trades source energy to accomplish tracking, i.e. if $A_1$ is the area of the energy pattern desired, and $A_2$ is the total area of the micromirror array illuminated by the source, the energy efficiency of the system is degraded by $A_1/A_2$. The key advantages of this approach include: that random energy application pattern shapes and rapid correction of location shifts can be accomplished much more rapidly than with conventional electromechanical systems.

An alternate implementation of this invention mounts the micromirrors on an electromechanical gimbal that is driven by the computer 14 to reduce the displacement relative to the workpiece index marks to an acceptably small error or zero. The advantage of this approach is to eliminate the efficiency loss cited above, since all of the energy illuminating the micromirrors is used within the predetermined pattern on the work piece.

Similarly, it is possible to accomplish the tracking by using other eletromechanical means including galvanometer mirror systems, and solenoid actuators.

Thin-film micromirror arrays 11 suitable for use in the present invention are made by Daewoo Electronics Co. Ltd. Korea under the trademark "Thin-film Micromirror Array (TMA).

The TMA, thin-film micromirror array 11, is an array of 1024×768 mirrors, each mirror measuring 49 microns×49 microns, with a panel size of 2.54 inches diagonal. The TMA is a reflective spatial modulator used to modulate light in television video projection. It is a suitable device for the ablation patterning with appropriate modifications to operate at UV wavelengths including UV grade optics and UV reflective mirrors.

Figure 9A:
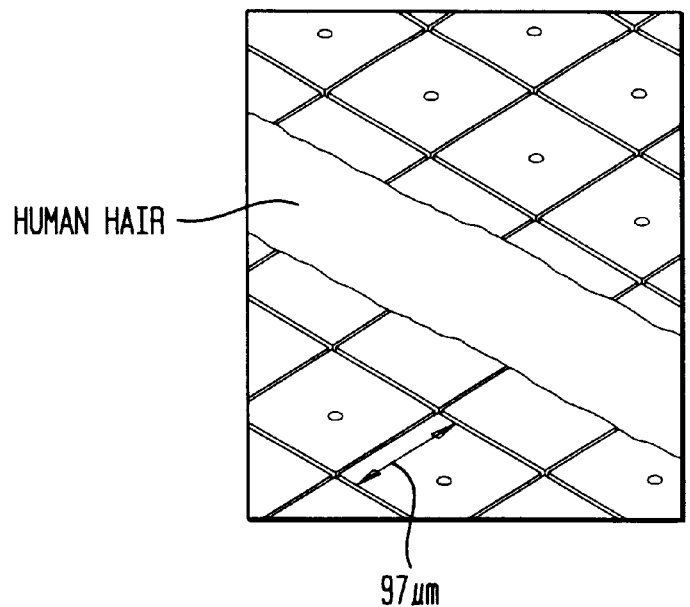
FIG. 9*a* is a photomicrograph of a TMA mirror array with a human hair superimposed to show scale.
Figure 9B:
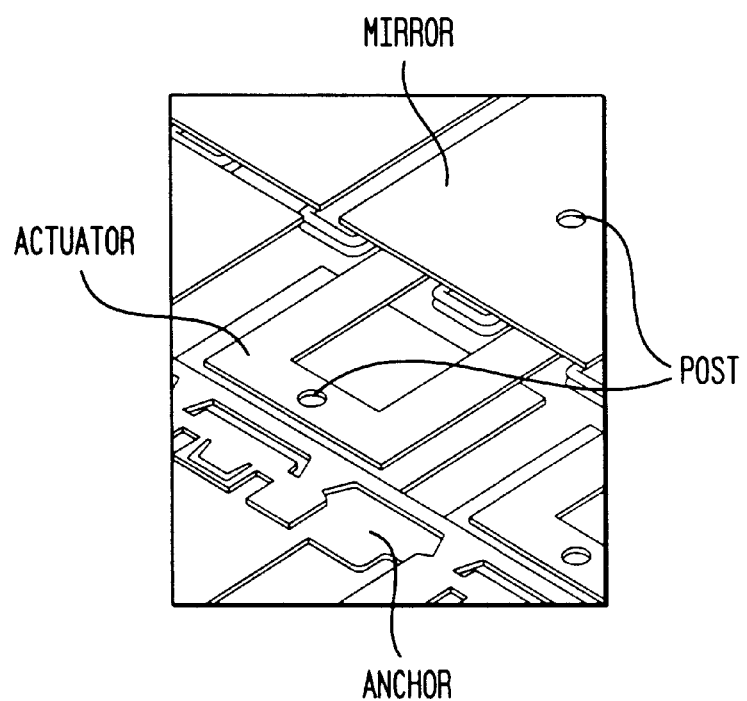
FIG. 9*b* shows the underlying actuator.
Figure 10:
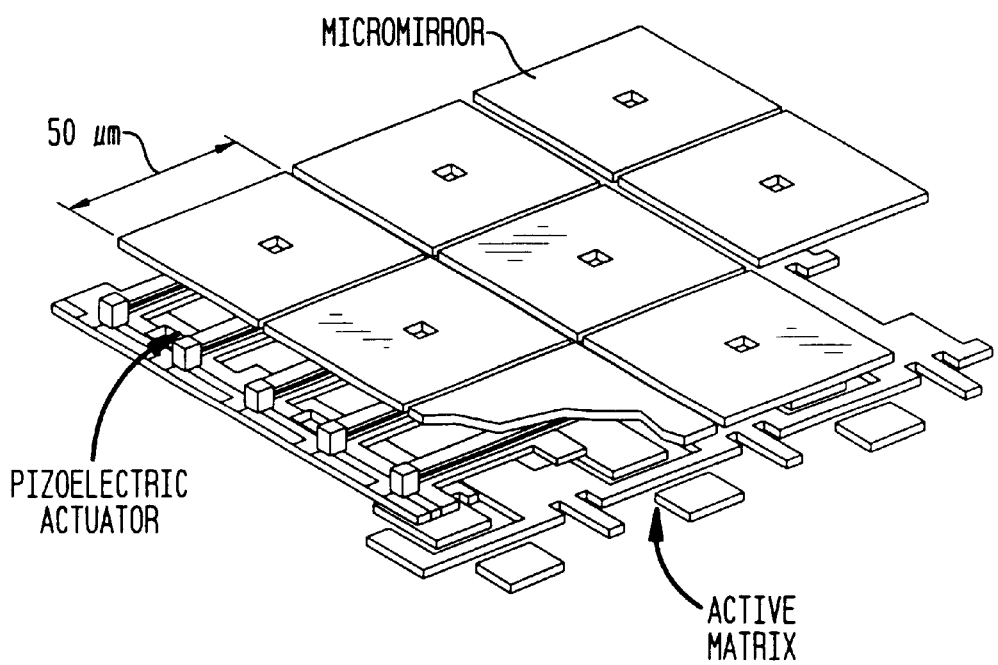
FIG. 10 is a schematic diagram of a TMA mirror array.

Each TMA pixel is a monolithically integrated MEMS (Microelectromechanical Systems) device fabricated over a simple PMOS switch as illustrated in FIG. 9a. The pixel size in this earlier version is 97 microns by 97 microns. Each pixel consists of a micromirror and an actuator as shown in FIG. 9b. Each aluminum mirror has high reflectivity and excellent flatness for high optical efficiency, and the actuator has linear and fast response times, as well as mechanical and electrical reliability. It is also understood that micromirror array 1 can be replaced by other reflective/transmissive mask devices including patterned foil devices. FIG. 10 illustrates the TMA array structure.

Figure 11:
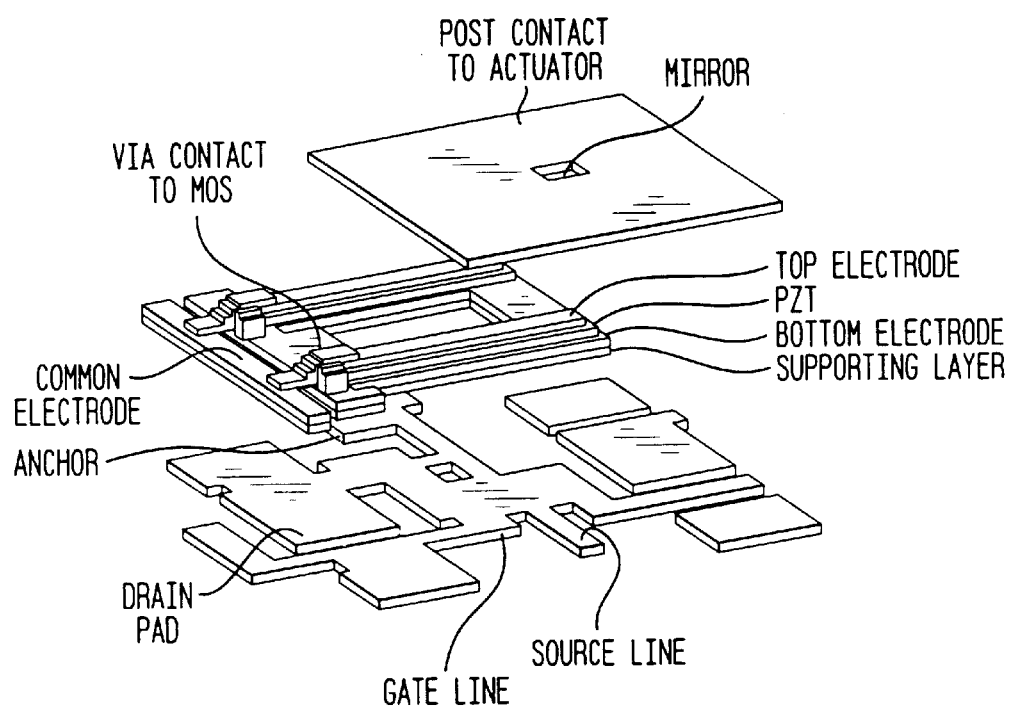
FIG. 11 is an exploded view of the TMA mirror array of FIG. 10.

The TMA uses thin film piezoelectric actuators in the form of micro-cantilevers. As shown in FIG. 11, a mirror is connected to the cantilevers themselves through a support post. The cantilevers themselves are anchored to the underlying substrate. A cantilever consists of the supporting layer, bottom electrode, piezoelectric layer, and top electrode. When an electric field is applied between the common electrode and the bottom electrode, the piezoelectric layer shrinks in the horizontal direction and expands in the vertical direction.

Figure 3A:
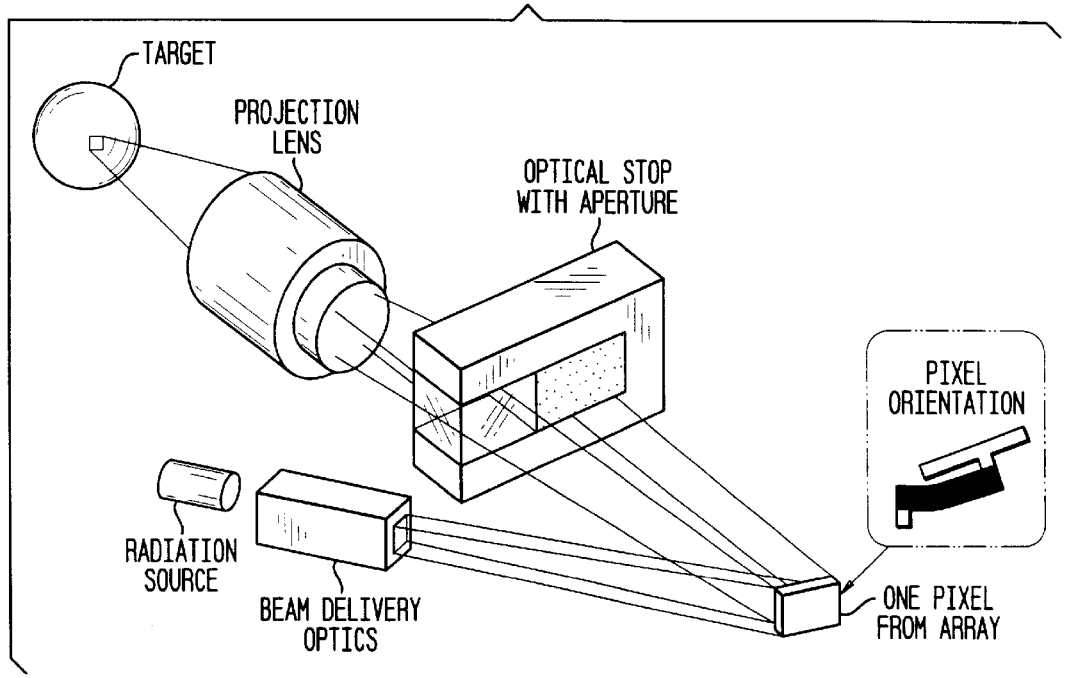
FIG. 3 illustrates the operation of a single partially deflected micromirror.
Figure 3B:
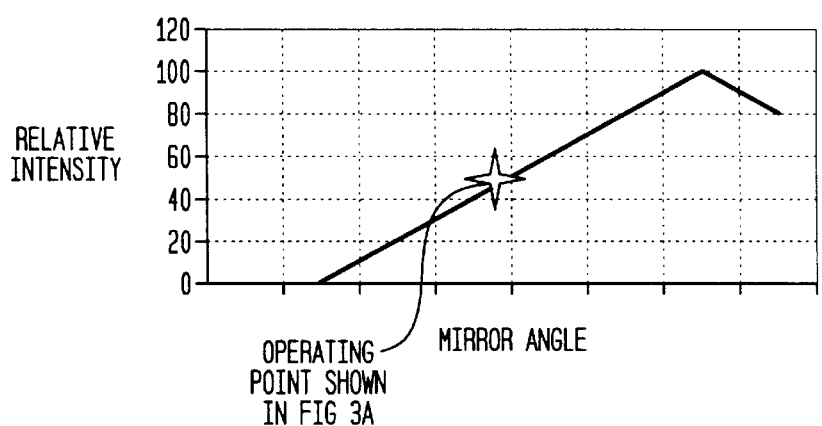
Figure 12:
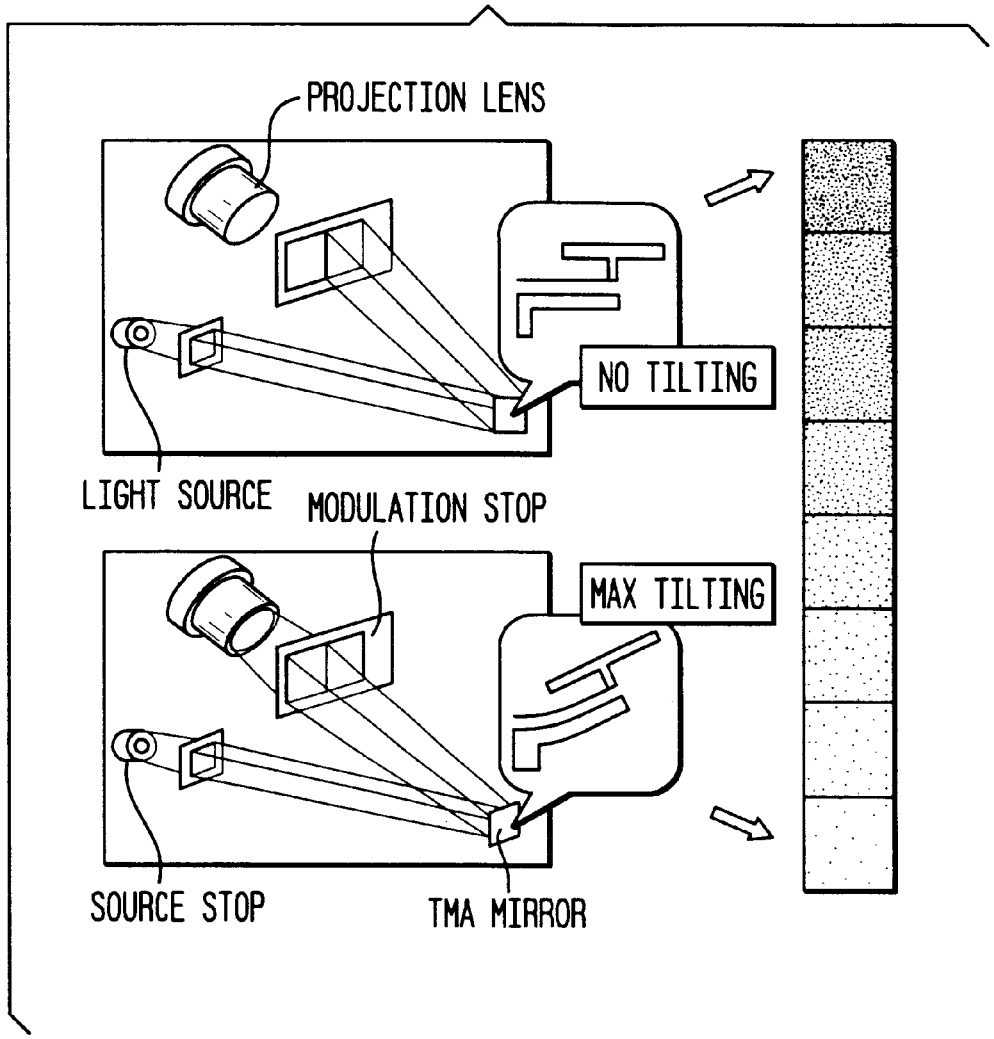
FIG. 12 illustrates the principle of light modulation by the TMA micromirror array.

Since the neutral plane of the cantilever shifts toward the bottom of the electrode due to thickness of the supporting layer, the mechanical strain of the piezoelectric layer causes vertical deflection of the cantilever and a tilt of the mirror on top of it. FIG. 12 shows the effect of tilting the mirror. When there is no tilt, no light goes out of the modulation stop and when maximum defection of the mirror is achieved, the maximum amount of light is passed by the modulation stop. FIGS. 2 and 3 detail the operation of one pixel in the undeflected and partially deflected positions. As is shown in graph 2b, the mirror deflection angle determines the amount of light that pass through the modulation or optical stop. In the case of the TMA, the piezoelectric material operates from 0 to 10 volts and the corresponding mirror deflection is from 0 to about 10 degrees.

It is also understood that other reflective mirror masks may be substituted for the micromirror array 11. Other micromirror array manufacturers include Texas Instruments (Dallas, Tex.) and Standard MEMS. One such system is a foil array of patterns, sequentially changed to modify the ablation etches on successive layers of a multi-layered structure as illustrated in FIGS. 6a and 6b. It is also understood that the work piece 30 may consist of tissue. One such tissue system is an eye, whose corneal tissue is ablated to modify its refractive properties, e.g. photorefractive keratectomy.

While the invention has been described with reference to the preferred embodiment thereof, it will be appreciated by those of ordinary skill in the art that modifications can be made to the structure and elements of the invention without departing from the spirit and scope of the invention as a whole.

What is claimed is:

1. A method for contouring the surface of a standard optical lens, said method comprising the steps of:
    (a) measuring the refractive error of a patient in need of a refractive correction;
    (b) providing the refractive function of said standard optical lens to a computer;
    (c) generating, using said computer, an electronic correction contour from a comparison of said refractive error relative to said refractive function;
    (d) transferring said electronic correction contour onto the surface of said lens by ablation etching with one or more laser pulses;
    (e) electronically measuring the refractive properties of said lens after each of said laser pulses;
    (f) comparing, by means of said computer, said refractive properties of said lens with said electronic correction contour;
    (g) terminating said ablation etching in localized areas wherein said refractive properties of said lens match said electronic correction contour.

2. The method of claim 1 wherein said ablation etching comprises the steps of:
    (h) generating a series of complex laser patterns by means of a micromirror array comprising a series of individually controllable micromirrors; and,
    (i) projecting said series of complex laser patterns onto the surface of said lens for the purpose of contouring said lens by successive ablation etchings.

3. The method of claim 2 wherein said micromirror array is a Thin-film.

4. The method of claim 1 wherein said ablation etching comprises the steps of:
    (j) generating a series of complex laser patterns by means of masks; and, (k) projecting said series of complex laser patterns onto the surface of said standard optical lens for the purpose of contouring said standard optical lens by successive ablation etchings.

5. The method of claim 4 wherein said masks are transmissive masks.

6. The method of claim 4 wherein said masks are printed reflective masks.

7. The method of claim 1 wherein said optical lens is a contact lens and wherein said electronic correction contour is an optimum visual acuity correction contour.

8. A method for contouring the surface of an eyeglass lens, said method comprising the steps of:
 (a) measuring the refractive error of a patient in need of a refractive correction;
 (b) generating, using a computer, an electronic correction contour from said refractive error;
 (c) transferring said electronic correction contour onto the surface of said eyeglass lens by ablation etching with one or more laser pulses;
 (d) electronically measuring the refractive properties of said lens after each of said laser pulses;
 (e) comparing, by means of said computer, said refractive properties of said lens with said electronic correction contour;
 (f) terminating said ablation etching in localized areas wherein said refractive properties of said lens match said electronic correction contour.

9. A method for contouring the surface of an optical lens, said method comprising the steps of:
 (a) measuring the refractive error of a patient in need of a refractive correction;
 (b) generating, using a computer, an electronic correction contour from said refractive error;
 (c) transferring said electronic correction contour onto the surface of said lens by ablation etching with one or more laser pulses wherein said ablation etching includes the steps of mounting said lens on a movable positioning table and moving said positioning table to change the position of said lens relative to an incident spot laser beam for the purpose of contouring said lens by successive ablation etchings;
 (d) electronically measuring the refractive properties of said lens after each of said laser pulses;
 (e) comparing, by means of said computer, said refractive properties of said lens with said electronic correction contour;
 (f) terminating said ablation etching in localized areas wherein said refractive properties of said lens match said electronic correction contour.

* * * * *